US012397195B2

(12) United States Patent
Lee

(10) Patent No.: US 12,397,195 B2
(45) Date of Patent: Aug. 26, 2025

(54) METHOD, DEVICE, AND NON-TRANSITORY COMPUTER-READABLE RECORDING MEDIUM FOR ESTIMATING INFORMATION REGARDING GOLF SWING

(71) Applicant: MOAIS, INC., Seoul (KR)

(72) Inventor: Yong Geun Lee, Seoul (KR)

(73) Assignee: MOAIS, INC., Seoul (KR)

( * ) Notice: Subject to any disclaimer, the term of this patent is extended or adjusted under 35 U.S.C. 154(b) by 321 days.

(21) Appl. No.: 18/108,832

(22) Filed: Feb. 13, 2023

(65) Prior Publication Data

US 2023/0181970 A1 Jun. 15, 2023

Related U.S. Application Data

(63) Continuation of application No. PCT/KR2021/010595, filed on Aug. 10, 2021.

(30) Foreign Application Priority Data

Aug. 31, 2020 (KR) .................. 10-2020-0110137

(51) Int. Cl.
*A63B 24/00* (2006.01)
*A63B 71/06* (2006.01)
(Continued)

(52) U.S. Cl.
CPC ...... *A63B 24/0003* (2013.01); *A63B 24/0062* (2013.01); *A63B 71/0622* (2013.01); *G06N 3/0464* (2023.01); *G06T 7/70* (2017.01); *G06T 7/97* (2017.01); *A63B 2102/32* (2015.10); *A63B 2220/05* (2013.01); *A63B 2220/807* (2013.01);
(Continued)

(58) Field of Classification Search
None
See application file for complete search history.

(56) References Cited

U.S. PATENT DOCUMENTS

| | | | |
|---|---|---|---|
| 5,111,410 A * | 5/1992 | Nakayama | A61B 5/1127 348/157 |
| 8,020,098 B2 * | 9/2011 | Katayama | G06V 40/23 715/722 |

(Continued)

FOREIGN PATENT DOCUMENTS

| | | |
|---|---|---|
| KR | 10-2009-0105031 A | 10/2009 |
| KR | 10-1428922 B1 | 8/2014 |

(Continued)

*Primary Examiner* — Seng H Lim
(74) *Attorney, Agent, or Firm* — Dinsmore & Shohl LLP; Yongsok Choi, Esq.

(57) ABSTRACT

A method for estimating information on a golf swing is provided. The method includes the steps of: estimating a three-dimensional position of at least one joint of a user, when two or more two-dimensional photographed images of the user's golf swing taken from different directions are acquired, by deriving probability information on a two-dimensional position of the at least one joint of the user from each of the two or more two-dimensional photographed images using an artificial neural network model, and combining the derived probability information on the two-dimensional position of the at least one joint; and estimating information on the user's golf swing with reference to the estimated three-dimensional position of the at least one joint.

11 Claims, 3 Drawing Sheets

(51) Int. Cl.
*G06N 3/0464* (2023.01)
*G06T 7/00* (2017.01)
*G06T 7/70* (2017.01)
*A63B 102/32* (2015.01)

(52) U.S. Cl.
CPC ........... *G06T 2207/20076* (2013.01); *G06T 2207/20084* (2013.01); *G06T 2207/30196* (2013.01); *G06T 2207/30221* (2013.01)

(56) References Cited

U.S. PATENT DOCUMENTS

| | | | | |
|---|---|---|---|---|
| 10,063,843 | B2* | 8/2018 | Yano | H04N 13/282 |
| 10,186,041 | B2* | 1/2019 | Chang | G06V 40/23 |
| 11,052,284 | B2* | 7/2021 | Suk | A63B 69/3623 |
| 2002/0114493 | A1* | 8/2002 | McNitt | A61B 5/1124 |
| | | | | 382/107 |
| 2002/0115047 | A1* | 8/2002 | McNitt | A63B 24/0003 |
| | | | | 434/252 |
| 2009/0005188 | A1* | 1/2009 | Iwatsubo | A63B 24/0021 |
| | | | | 473/409 |
| 2012/0088544 | A1* | 4/2012 | Bentley | A63F 13/332 |
| | | | | 455/556.1 |
| 2016/0296795 | A1* | 10/2016 | Chang | G06T 7/20 |
| 2020/0074165 | A1* | 3/2020 | Ghafoor | G06V 40/103 |
| 2020/0406098 | A1* | 12/2020 | Bartholomew | A63B 71/0622 |
| 2021/0315486 | A1* | 10/2021 | Delp | G16H 50/50 |
| 2021/0409656 | A1* | 12/2021 | Imes | A63B 69/3691 |
| 2022/0273998 | A1* | 9/2022 | Park | G06V 10/26 |
| 2022/0400202 | A1* | 12/2022 | Imes | H04N 5/77 |
| 2023/0126755 | A1* | 4/2023 | Yamashita | G06T 7/74 |
| | | | | 382/103 |
| 2023/0401736 | A1* | 12/2023 | Lee | G06T 7/70 |

FOREIGN PATENT DOCUMENTS

| | | |
|---|---|---|
| KR | 10-2016-0121379 A | 10/2016 |
| KR | 10-2019-0019824 A | 2/2019 |

* cited by examiner

METHOD, DEVICE, AND NON-TRANSITORY COMPUTER-READABLE RECORDING MEDIUM FOR ESTIMATING INFORMATION REGARDING GOLF SWING

CROSS-REFERENCE TO RELATED APPLICATION(S)

This application is a continuation application of Patent Cooperation Treaty (PCT) International Application No. PCT/KR2021/010595 filed on Aug. 10, 2021, which claims priority to Korean Patent Application No. 10-2020-0110137 filed on Aug. 31, 2020. The entire contents of PCT International Application No. PCT/KR2021/010595 and Korean Patent Application No. 10-2020-0110137 are hereby incorporated by reference.

FIELD OF THE INVENTION

The present invention relates to a method, device, and non-transitory computer-readable recording medium for estimating information on a golf swing.

BACKGROUND

Recently, techniques for analyzing images of a golfer's swing and providing useful information to the golfer have been introduced.

As an example of related conventional techniques, Korean Laid-Open Patent Publication No. 2009-105031 discloses a golf clinic system employing image processing techniques and an operation method thereof, the system comprising: a plurality of markers attached to a body and a golf club of a golf practitioner; a plurality of cameras for collecting images of a swing motion of the golf practitioner; an image analyzer for reconstructing two-dimensional images collected from the plurality of cameras into three-dimensional images, extracting spatial coordinates of the markers according to movements, and analyzing angular values of parts of the body and data for each stage in real time to output a clinic result in a report format; and a database in which kinematic clinic information on the swing motion is matched with member information and stored as digital data.

However, according to the techniques introduced so far as well as the above-described conventional technique, it is necessary to separately use an expensive instrument for recognizing a golfer's posture and motion, or to attach separate sensors (or markers) to the golfer's body and golf club, in order to analyze the golfer's swing.

SUMMARY OF THE INVENTION

One object of the present invention is to solve all the above-described problems in prior art.

Another object of the invention is to estimate a three-dimensional position of at least one joint of a user, when two or more two-dimensional photographed images of the user's golf swing taken from different directions are acquired, by deriving probability information on a two-dimensional position of the at least one joint of the user from each of the two or more two-dimensional photographed images using an artificial neural network model, and combining the derived probability information on the two-dimensional position of the at least one joint, and estimate information on the user's golf swing with reference to the estimated three-dimensional position of the at least one joint.

Yet another object of the invention is to light-weight an artificial neural network model using depthwise convolution and pointwise convolution, and estimate at least one joint of a user from a photographed image of the user's golf swing using the light-weighted artificial neural network model.

The representative configurations of the invention to achieve the above objects are described below.

According to one aspect of the invention, there is provided a method comprising the steps of: estimating a three-dimensional position of at least one joint of a user, in response to acquiring two or more two-dimensional photographed images of the user's golf swing taken from different directions, by deriving probability information on a two-dimensional position of the at least one joint of the user from each of the two or more two-dimensional photographed images using an artificial neural network model, and combining the derived probability information on the two-dimensional position of the at least one joint; and estimating information on the user's golf swing with reference to the estimated three-dimensional position of the at least one joint.

According to another aspect of the invention, there is provided a device comprising: a position information management unit configured to estimate a three-dimensional position of at least one joint of a user, in response to acquiring two or more two-dimensional photographed images of the user's golf swing taken from different directions, by deriving probability information on a two-dimensional position of the at least one joint of the user from each of the two or more two-dimensional photographed images using an artificial neural network model, and combining the derived probability information on the two-dimensional position of the at least one joint; and a swing information estimation unit configured to estimate information on the user's golf swing with reference to the estimated three-dimensional position of the at least one joint.

In addition, there are further provided other methods and devices to implement the invention, as well as non-transitory computer-readable recording media having stored thereon computer programs for executing the methods.

According to the invention, it is possible to estimate a three-dimensional position of at least one joint of a user, when two or more two-dimensional photographed images of the user's golf swing taken from different directions are acquired, by deriving probability information on a two-dimensional position of the at least one joint of the user from each of the two or more two-dimensional photographed images using an artificial neural network model, and combining the derived probability information on the two-dimensional position of the at least one joint, and estimate information on the user's golf swing with reference to the estimated three-dimensional position of the at least one joint, thereby estimating the information on the user's golf swing only from the photographed images, without using any separate sensor or instrument.

According to the invention, it is possible to light-weight an artificial neural network model using depthwise convolution and pointwise convolution, and estimate at least one joint's position of a user from a two-dimensional photographed image of the user's golf swing using the light-weighted artificial neural network model in a mobile device, thereby accurately and efficiently estimating information on the user's golf swing in the mobile device, without using any separate sensor or instrument.

DETAILED DESCRIPTION

Figure 1:
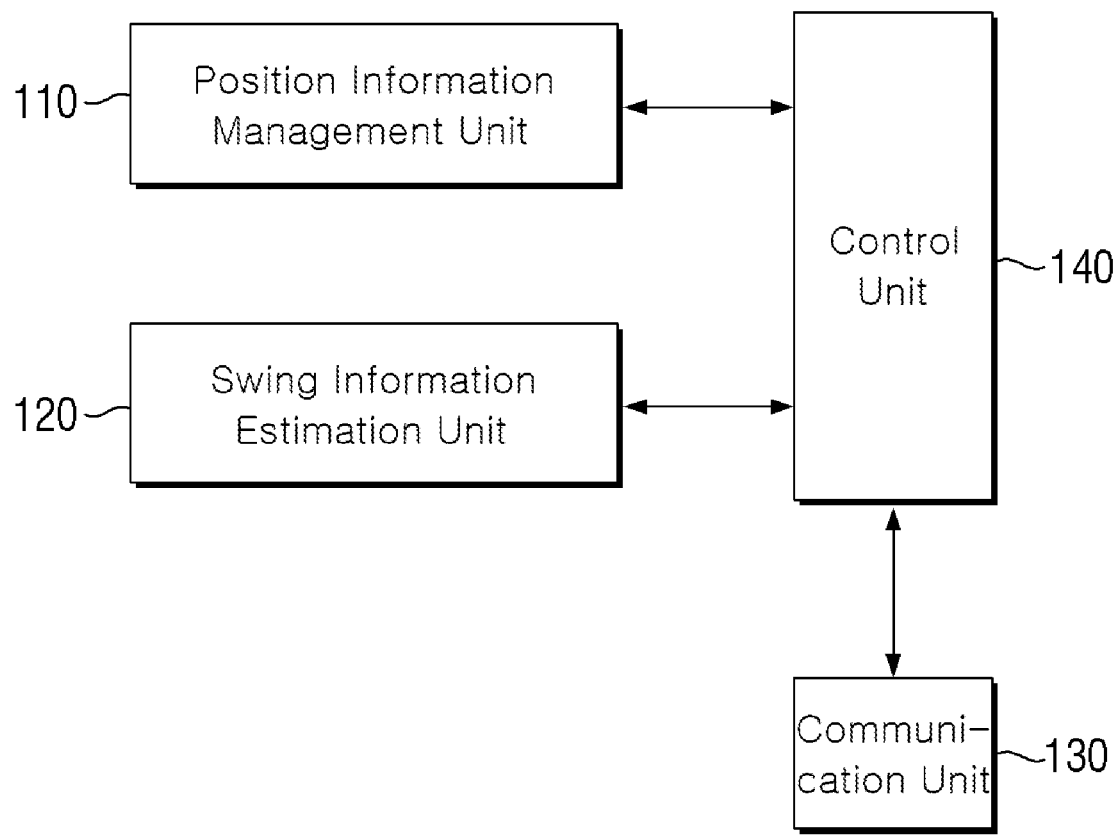
FIG. 1 specifically shows the internal configuration of a device according to one embodiment of the invention.

In the following detailed description of the present invention, references are made to the accompanying drawings that show, by way of illustration, specific embodiments in which the invention may be practiced. These embodiments are described in sufficient detail to enable those skilled in the art to practice the invention. It is to be understood that the various embodiments of the invention, although different from each other, are not necessarily mutually exclusive. For example, specific shapes, structures, and characteristics described herein may be implemented as modified from one embodiment to another without departing from the spirit and scope of the invention. Furthermore, it shall be understood that the positions or arrangements of individual elements within each embodiment may also be modified without departing from the spirit and scope of the invention. Therefore, the following detailed description is not to be taken in a limiting sense, and the scope of the invention is to be taken as encompassing the scope of the appended claims and all equivalents thereof. In the drawings, like reference numerals refer to the same or similar elements throughout the several views.

Hereinafter, various preferred embodiments of the present invention will be described in detail with reference to the accompanying drawings to enable those skilled in the art to easily implement the invention.

Although embodiments related to a golf swing are described herein focusing on a full swing, the golf swing according to the invention should be understood in the broadest sense as encompassing all motions for moving a golf club. For example, the golf swing according to one embodiment of the invention may include a full swing, a half swing, a chip shot, a lobe shot, and a putt.

Although the descriptions herein are focused on golf, it will be apparent to those skilled in the art that the present invention may be utilized even for estimating information on motions performed in sports other than golf. For example, the present invention may be utilized for estimating information on a baseball swing or information on a workout or yoga posture.

Configuration of a Device

Hereinafter, the internal configuration of a device 100 crucial for implementing the invention and the functions of the respective components thereof will be discussed.

FIG. 1 specifically shows the internal configuration of the device 100 according to one embodiment of the invention.

As shown in FIG. 1, the device 100 according to one embodiment of the invention may comprise a position information management unit 110, a swing information estimation unit 120, a communication unit 130, and a control unit 140. According to one embodiment of the invention, at least some of the position information management unit 110, the swing information estimation unit 120, the communication unit 130, and the control unit 140 may be program modules to communicate with an external system (not shown). The program modules may be included in the device 100 in the form of operating systems, application program modules, or other program modules, while they may be physically stored in a variety of commonly known storage devices. Further, the program modules may also be stored in a remote storage device that may communicate with the device 100. Meanwhile, such program modules may include, but are not limited to, routines, subroutines, programs, objects, components, data structures, and the like for performing specific tasks or executing specific abstract data types as will be described below in accordance with the invention.

Meanwhile, the above description is illustrative although the device 100 has been described as above, and it will be apparent to those skilled in the art that at least a part of the components or functions of the device 100 may be implemented in a server (not shown) or included in an external system (not shown), as necessary.

Meanwhile, the device 100 according to one embodiment of the invention is digital equipment having a memory means and a microprocessor for computing capabilities, and may include smart phones, tablets, smart watches, smart bands, smart glasses, desktop computers, notebook computers, workstations, personal digital assistants (PDAs), web pads, and mobile phones. However, the device 100 is not limited to the examples mentioned above, and may be changed without limitation as long as the objects of the invention may be achieved.

In particular, the device 100 may include an application (not shown) for assisting a user to receive services such as estimation of information on a golf swing from the device 100. The application may be downloaded from an external application distribution server (not shown). Meanwhile, the characteristics of the application may be generally similar to those of the position information management unit 110, the swing information estimation unit 120, the communication unit 130, and the control unit 140 of the device 100 to be described below. Here, at least a part of the application may be replaced with a hardware device or a firmware device that may perform a substantially equal or equivalent function, as necessary.

First, the position information management unit 110 according to one embodiment of the invention may function to acquire two or more two-dimensional photographed images of a user's golf swing taken from different directions.

Specifically, according to one embodiment of the invention, the two or more two-dimensional photographed images of the user's golf swing taken from different directions may be photographed by two or more devices 100, or may be photographed by another device (not shown) and acquired by the device 100. Further, according to one embodiment of the invention, the two or more two-dimensional photographed images of the user's golf swing taken from different directions may be images photographed by RGB cameras. That is, the position information management unit 110 according to one embodiment of the invention may estimate a three-dimensional position of at least one joint of the user using only the two or more two-dimensional photographed images of the user's golf swing taken from different directions, without using depth information acquired from an instrument such as a depth camera or a depth sensor. Meanwhile, a two-dimensional photographed image according to the invention mainly refers to a moving picture, but should be understood in the broadest sense as encompassing all data that may represent a user's golf swing in visual forms regardless of their formats.

Further, the position information management unit 110 according to one embodiment of the invention may function to derive probability information on a two-dimensional position of the at least one joint of the user from each of the two or more two-dimensional photographed images of the user's golf swing taken from different directions using an artificial neural network model.

Specifically, the probability information on the two-dimensional position of the at least one joint of the user derived by the position information management unit 110 according to one embodiment of the invention may be included in a two-dimensional probability map (i.e., output data of the artificial neural network model) generated by using each of the two or more two-dimensional photographed images of the user's golf swing taken from different directions as input data of the artificial neural network model.

For example, according to one embodiment of the invention, the two-dimensional probability map may be a two-dimensional heat map. Further, the position information management unit 110 according to one embodiment of the invention may generate at least one two-dimensional heat map image for each of the at least one joint of the user using the artificial neural network model, and may derive the probability information on the two-dimensional position of the at least one joint of the user on the basis of properties such as the two-dimensional position of the at least one joint being more likely to correspond to pixels with larger values, among pixels constituting the generated at least one heat map image, or the position of the at least one joint being less likely to be accurately specified as pixels with small values are widely distributed in the heat map, and being more likely to be accurately specified as pixels with large values are narrowly distributed in the heat map.

Meanwhile, the at least one joint of the user for which the probability information on the two-dimensional position is derived by the position information management unit 110 according to one embodiment of the invention may be joints essentially required for estimating information on the user's golf swing. That is, when the information on the user's golf swing is estimated, the computational efficiency of the artificial neural network model may be improved by limiting the number of joints to be detected such that joints of relatively low importance are not detected.

Meanwhile, the artificial neural network model according to one embodiment of the invention may include, for example, a convolutional neural network (CNN) model, a recurrent neural network (RNN) model, a deep belief network (DBN) model, or an artificial neural network model in which the foregoing models are combined. However, the artificial neural network model according to one embodiment of the invention is not limited to those mentioned above, and may be diversely changed as long as the objects of the invention may be achieved.

Further, the artificial neural network model according to one embodiment of the invention may be a model that is light-weighted using depthwise convolution and pointwise convolution.

In addition, the artificial neural network model according to one embodiment of the invention may be a model that is light-weighted using a light-weighting algorithm such as pruning, weight quantization, and residual learning.

Specifically, since artificial neural network models commonly used in object recognition technology require a high level of computing resources to be consumed for a high level of recognition performance, it is often difficult to use such models in environments where only limited computing resources are provided (e.g., mobile devices). Therefore, according to one embodiment of the invention, an artificial neural network model may be light-weighted using depthwise convolution and pointwise convolution, and the light-weighted artificial neural network model may be used in a mobile device so that at least one joint of a user may be detected from a photographed image of the user's golf swing.

Here, the depthwise convolution according to one embodiment of the invention may refer to a convolution process in which a kernel is applied for each depth (i.e., each channel) of an input layer, in performing convolution in the artificial neural network model according to one embodiment of the invention. Meanwhile, since the method of operation using the applied kernel is the same as that of general convolution, a detailed description thereof will be omitted.

Further, the pointwise convolution according to one embodiment of the invention may refer to a convolution process in which a kernel of size $1 \times 1 \times M$ (i.e., a kernel of width 1, height 1, and depth M) is applied for each point of an input layer, in performing convolution in the artificial neural network model according to one embodiment of the invention.

Figure 2A:
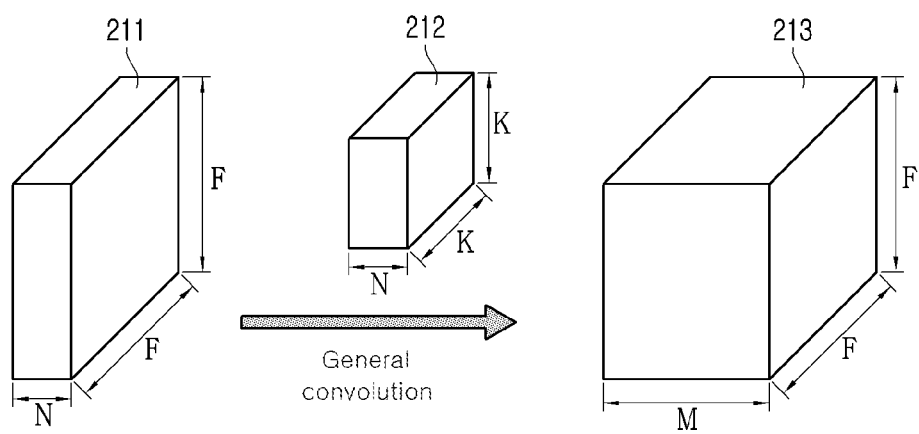
FIG. 2A illustratively shows how general convolution is performed according to one embodiment of the invention.

FIG. 2A illustratively shows how general convolution is performed according to one embodiment of the invention.

Figure 2B:
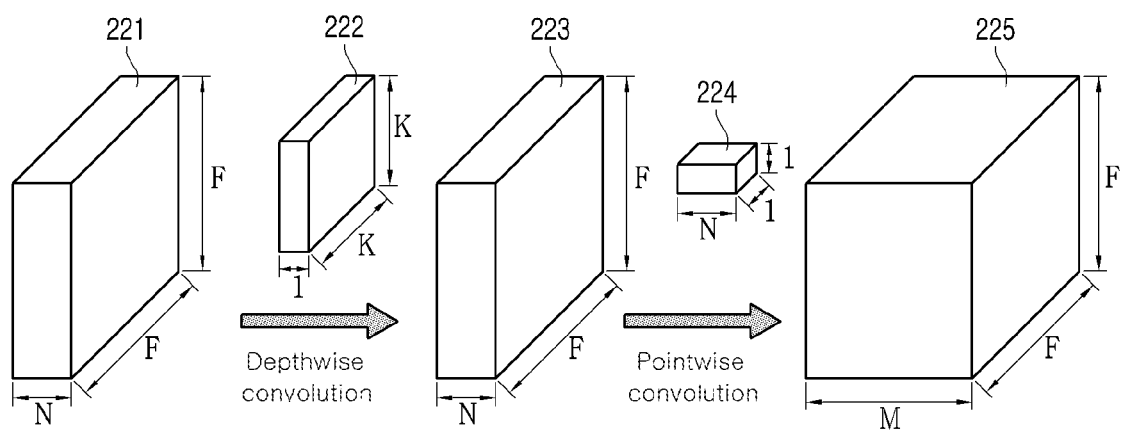
FIG. 2B illustratively shows how depthwise convolution and pointwise convolution are performed according to one embodiment of the invention.

FIG. 2B illustratively shows how depthwise convolution and pointwise convolution are performed according to one embodiment of the invention.

Referring to FIG. 2A, according to one embodiment of the invention, it may be assumed that the width, height, and depth of an input layer 211 are F, F, and N, respectively; the width, height, and depth of each kernel 212 are K, K, and N, respectively; and the width, height, and depth of an output layer 213 are F, F, and M, respectively. Here, it is assumed that padding and stride are appropriately sized such that there is no change in the width and height of the input layer 211 and the output layer 213. In this case, in the general convolution, the kernel 212 is applied to the input layer 211 to constitute one depth of the output layer 213 (through $F \times F \times K \times K \times N$ operations), and these operations are performed for M kernels 212 so that a total of $F \times F \times K \times K \times N \times M$ operations are performed.

Referring to FIG. 2B, according to one embodiment of the invention, it may be assumed that the width, height, and depth of an input layer 221 are F, F, and N, respectively; the width, height, and depth of each kernel 222 in the depthwise convolution are K, K, and 1, respectively; the width, height, and depth of each kernel 224 in the pointwise convolution are 1, 1, and N, respectively; and the width, height and depth of an output layer 225 are F, F, and M, respectively. In this case, the kernel 222 is applied for each depth of the input layer 221 to constitute each depth of an intermediate layer 223 (through $F \times F \times K \times K \times 1 \times N$ operations). Then, the kernel 224 is applied for each point of the intermediate layer 223 to constitute one depth of the output layer 225 (through $F \times F \times 1 \times 1 \times N$ operations), and these operations are performed for M kernels 224 so that a total of $F \times F \times 1 \times 1 \times N \times M$ operations are performed in the pointwise convolution. Therefore, according to one embodiment of the invention, a total of $(F \times F \times K \times K \times 1 \times N) + (F \times F \times 1 \times 1 \times N \times M)$ operations are performed in the depthwise convolution and the pointwise convolution, so that the amount of operations is reduced compared to the general convolution.

Meanwhile, the light-weighting algorithms according to one embodiment of the invention are not necessarily limited to the above algorithms (i.e., the depthwise convolution and the pointwise convolution), and the order or number of times of applying each of the above algorithms may also be diversely changed.

Further, the position information management unit 110 according to one embodiment of the invention may function to estimate a three-dimensional position of the at least one joint of the user by combining the probability information on the two-dimensional position of the at least one joint of the user derived from each of the two or more two-dimensional photographed images of the user's golf swing taken from different directions.

Specifically, according to one embodiment of the invention, the derived probability information on the two-dimensional position of the at least one joint of the user may be included in a two-dimensional probability map (e.g., a two-dimensional heat map) for each of the two or more two-dimensional photographed images. Further, the position information management unit 110 according to one embodiment of the invention may estimate the three-dimensional position of the at least one joint of the user with reference to a three-dimensional probability map (e.g., a three-dimensional heat map) generated by projecting each of the two-dimensional probability maps into one three-dimensional space.

More specifically, when the two or more two-dimensional photographed images of the user's golf swing taken from different directions are acquired, the position information management unit 110 according to one embodiment of the invention may acquire information on a position in which each of the images is taken (or a distance from the user to the device by which the image is taken), a direction in which each of the images is taken (e.g., the user's front or side is photographed), and the like together. Further, the position information management unit 110 according to one embodiment of the invention may project each of the two-dimensional probability maps into one three-dimensional space on the basis of the above information, thereby generating a three-dimensional probability map in which the derived probability information on the two-dimensional position of the at least one joint of the user is combined.

Here, according to one embodiment of the invention, the information on the position and direction in which each of the two or more two-dimensional photographed images of the user's golf swing taken from different directions is taken may be relative values (or relative values calculated on the basis of absolute values). That is, the position information management unit 110 according to one embodiment of the invention may acquire information on relative positions and directions of two or more cameras that take the two or more two-dimensional photographed images, respectively. According to one embodiment of the invention, this information may be acquired with reference to a checkerboard image for each of the two or more two-dimensional photographed images, and the position information management unit 110 according to one embodiment of the invention may perform calibration for generating the three-dimensional probability map on the basis of the information.

Further, it should be understood that according to one embodiment of the invention, the three-dimensional probability map generated as above is generated by projecting the two-dimensional probability maps into a three-dimensional space, rather than by projecting the two-dimensional position itself (i.e., two-dimensional coordinates) of the at least one joint of the user into a three-dimensional space. This allows an image from which the position of the at least one joint of the user is more likely to be accurately estimated, among the two or more two-dimensional photographed images of the user's golf swing taken from different directions, to be preferentially considered over an image from which the position of the at least one joint of the user is less likely to be accurately estimated, and consequently allows the three-dimensional position of the at least one joint of the user to be more accurately estimated.

In addition, the position information management unit 110 according to one embodiment of the invention may estimate the three-dimensional position of the at least one joint of the user by using the generated three-dimensional probability map as input data of an artificial neural network model capable of three-dimensional operations. For example, according to one embodiment of the invention, the artificial neural network model capable of three-dimensional operations may include, but is not limited to, a voxel-to-voxel (V2V) network capable of three-dimensional convolution operations.

Meanwhile, the position information management unit 110 according to one embodiment of the invention estimates the three-dimensional position of the at least one joint of the user not necessarily by projecting the two-dimensional probability maps into a three-dimensional space, and the manner of estimation may be diversely changed as long as the objects of the invention may be achieved.

For example, according to one embodiment of the invention, the three-dimensional position of the at least one joint of the user may be estimated on the basis of the two-dimensional position itself (i.e., two-dimensional coordinates) of the at least one joint of the user estimated from the two-dimensional probability map (e.g., two-dimensional heat map) for each of the two or more two-dimensional photographed images, and the position information and direction information of each of the two or more cameras, in a manner that the two-dimensional position of the at least one joint more accurately estimated from the two-dimensional photographed images is more reflected in a result of estimating the three-dimensional position of the at least one joint, with reference to values of the two-dimensional probability maps.

Meanwhile, the position information management unit 110 according to one embodiment of the invention may combine the probability information on the two-dimensional position of the at least one joint of the user derived from each of the two or more two-dimensional photographed images of the user's golf swing taken from different directions, after the two or more two-dimensional photographed images are synchronized.

Specifically, the position information management unit 110 according to one embodiment of the invention may synchronize the two or more two-dimensional photographed images by frames, so that at least one frame constituting each of the two or more two-dimensional photographed images may be matched and coupled with a frame taken at the same time as the at least one frame. To this end, the position information management unit 110 according to one embodiment of the invention may acquire information on times of taking the two or more two-dimensional photographed images.

Further, the position information management unit 110 according to one embodiment of the invention may estimate at least one of a type of the at least one joint of the user, a position of the at least one joint of the user, a distance between the at least one joint of the user and at least one other joint of the user, and an angle formed between the at least one joint of the user and at least one other joint of the user, on the basis of the probability information on the two-dimensional position of the at least one joint of the user derived from each of the two or more two-dimensional photographed images of the user's golf swing taken from different directions, and may estimate a posture of the user (which may be less accurate than a posture estimated on the basis of the three-dimensional position of the at least one joint to be described below) on the basis of the foregoing. In addition, the position information management unit 110 according to one embodiment of the invention may cause storage of each of the two-dimensional photographed images to be started when the estimated posture of the user satisfies a predetermined storage start condition, and may cause the storage of each of the two-dimensional photographed images to be ended when the estimated posture of the user satisfies a predetermined storage end condition.

Furthermore, at least one of a predetermined storage start condition and a predetermined storage end condition according to one embodiment of the invention may be displayed on the device 100 in the form of guide lines and provided to the user. In addition, according to one embodiment of the invention, the storage start condition and the storage end condition may be determined in the form of voice commands.

Figure 3:
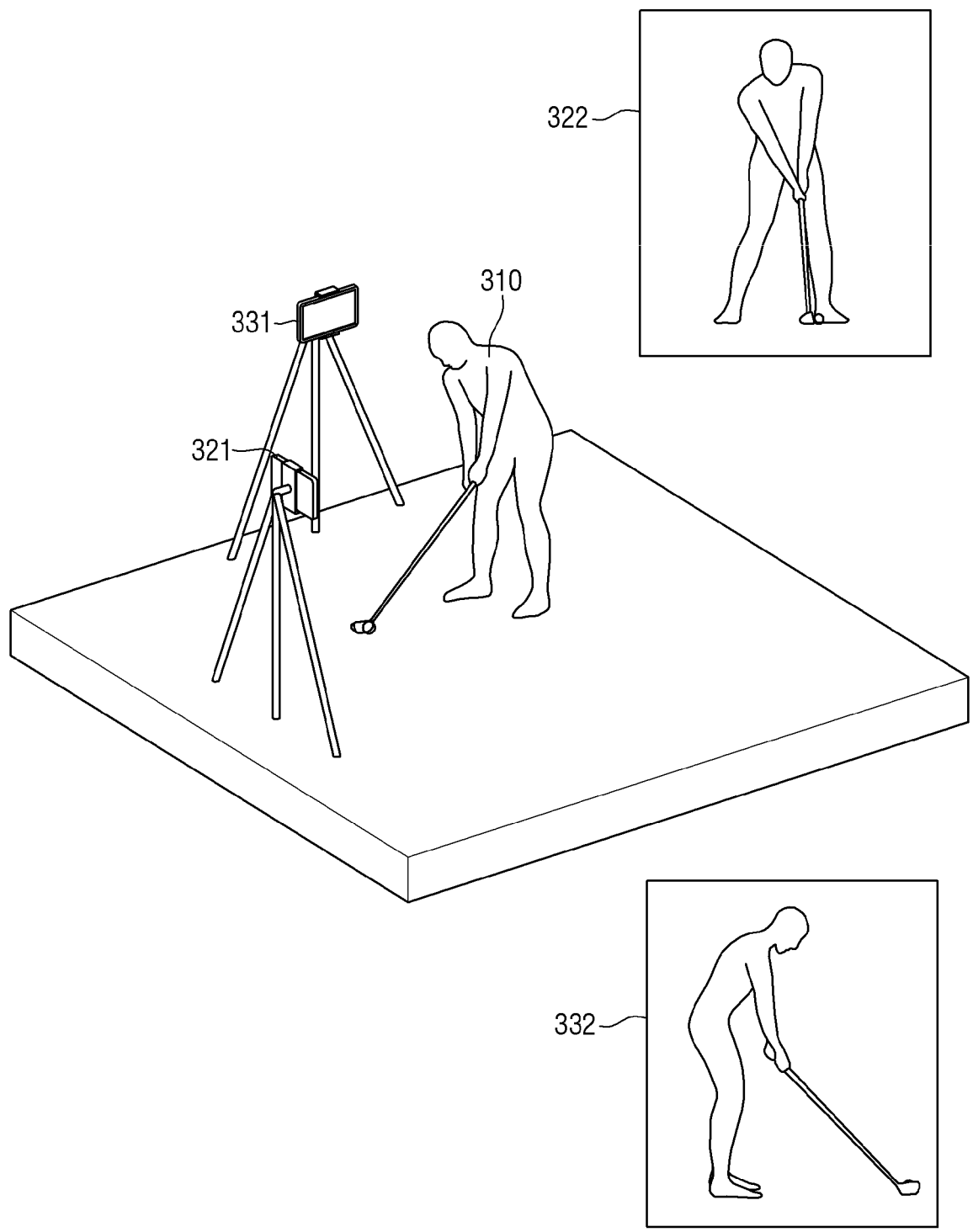
FIG. 3 illustratively shows how to estimate information on a user's golf swing according to one embodiment of the invention.

FIG. 3 illustratively shows how to estimate information on a user's golf swing according to one embodiment of the invention.

Referring to FIG. 3, according to one embodiment of the invention, a first device 321 may acquire a two-dimensional photographed image 322 of a golf swing of a user 310 taken from a first direction. Further, a second device 331 may acquire a two-dimensional photographed image 332 of the golf swing of the user 310 taken from a second direction.

Referring further to FIG. 3, according to one embodiment of the invention, the first device 321 and the second device 331 may derive probability information on a two-dimensional position of at least one joint of the user 310 from the acquired two-dimensional photographed images 322 and 332 using an artificial neural network model, respectively.

Referring further to FIG. 3, according to one embodiment of the invention, the first device 321 and the second device 331 may estimate a posture of the user 310 on the basis of the derived probability information on the two-dimensional position of the at least one joint, respectively. Further, according to one embodiment of the invention, the first device 321 and the second device 331 may cause storage of the acquired two-dimensional photographed images 322 and 332 to be started when the estimated posture of the user 310 satisfies a predetermined storage start condition (e.g., a swing preparation motion is started), respectively, and may cause the storage of the acquired two-dimensional photographed images 322 and 332 to be ended when the estimated posture of the user 310 satisfies a predetermined storage end condition (e.g., a predetermined amount of time elapses after a finish motion is ended), respectively.

Referring further to FIG. 3, the position information management unit 110 according to one embodiment of the invention may synchronize the two-dimensional photographed images 322 and 332 by frames, so that at least one frame constituting each of the two-dimensional photographed images 322 and 332 may be matched and coupled with a frame taken at the same time as the at least one frame.

For example, according to one embodiment of the invention, the first device 321 may acquire, from the second device 331, information on a time of taking the two-dimensional photographed image 332 taken from the second direction (which may include information on a time of taking at least one frame constituting the two-dimensional photographed image 332). Further, the position information management unit 110 according to one embodiment of the invention may synchronize at least one frame constituting each of the two-dimensional photographed images 322 and 332 by frames, with reference to the acquired information on the time. Here, a part of the two-dimensional photographed images 322 and 332 may be cropped in order to perform the synchronization.

Meanwhile, the position information management unit 110 according to one embodiment of the invention may function to estimate a three-dimensional position of a golf club by deriving probability information on a two-dimensional position of the golf club from each of the two or more two-dimensional photographed images of the user's golf swing taken from different directions using the artificial neural network model, and combining the derived probability information on the two-dimensional position of the golf club. Since this function may be performed in the same manner as the function of estimating the position of the at least one joint of the user as described in detail above, a detailed description thereof will be omitted.

Next, the swing information estimation unit 120 according to one embodiment of the invention may function to estimate information on the user's golf swing with reference to the three-dimensional position of the at least one joint of the user estimated by the position information management unit 110 according to one embodiment of the invention.

Specifically, the swing information estimation unit 120 according to one embodiment of the invention may estimate at least one of a type of the at least one joint of the user, a position of the at least one joint of the user, a distance between the at least one joint of the user and at least one other joint of the user, and an angle formed between the at least one joint of the user and at least one other joint of the user, on the basis of the three-dimensional position of the at least one joint of the user, and may estimate a posture of the user on the basis of the foregoing. Further, the swing information estimation unit 120 according to one embodiment of the invention may estimate the information on the user's golf swing on the basis of the estimated posture of the user.

Here, the information on the user's golf swing according to one embodiment of the invention may include information on the user's swing speed, swing tempo, swing plane, cocking, and swing posture (e.g., information on the user's head-up, sway, and early extension). However, the information on the user's golf swing according to one embodiment of the invention is not limited to those listed above, and may be diversely changed as long as the objects of the invention may be achieved.

Meanwhile, the swing information estimation unit 120 according to one embodiment of the invention may estimate the information on the user's golf swing with further reference to the three-dimensional position of the golf club that may be estimated by the position information management unit 110 according to one embodiment of the invention. Further, according to one embodiment of the invention, information on the golf club may include, but is not limited to, a position of the golf club and an angle formed by a body part of the user and the golf club.

Meanwhile, according to one embodiment of the invention, the information on the user's golf swing may be estimated separately for each partial motion constituting the golf swing.

Specifically, the golf swing according to one embodiment of the invention may be composed of eight stages of partial motions such as an address, a takeaway, a back swing, a top-of-swing, a down swing, an impact, a follow-through, and a finish. Further, the swing information estimation unit 120 according to one embodiment of the invention may derive to which of the above eight stages the two-dimensional photographed image of the user's golf swing corresponds, with reference to the three-dimensional position of the at least one joint of the user estimated by the position information management unit 110 according to one embodiment of the invention, and may estimate the information on the user's golf swing separately for each partial motion constituting the golf swing.

Meanwhile, the golf swing according to one embodiment of the invention is not necessarily separated into the eight stages as described above. That is, it may be separated to further include detailed stages constituting each of the eight stages, or such that at least some of the eight stages constitute one stage.

Next, the communication unit 130 according to one embodiment of the invention may function to enable data transmission/reception from/to the position information management unit 110 and the swing information estimation unit 120.

Lastly, the control unit 140 according to one embodiment of the invention may function to control data flow among the position information management unit 110, the swing information estimation unit 120, and the communication unit 130. That is, the control unit 140 according to the invention may control data flow into/out of the device 100 or data flow among the respective components of the device 100, such that the position information management unit 110, the swing information estimation unit 120, and the communication unit 130 may carry out their particular functions, respectively.

The embodiments according to the invention as described above may be implemented in the form of program instructions that can be executed by various computer components, and may be stored on a computer-readable recording medium. The computer-readable recording medium may include program instructions, data files, and data structures, separately or in combination. The program instructions stored on the computer-readable recording medium may be specially designed and configured for the present invention, or may also be known and available to those skilled in the computer software field. Examples of the computer-readable recording medium include the following: magnetic media such as hard disks, floppy disks and magnetic tapes; optical media such as compact disk-read only memory (CD-ROM) and digital versatile disks (DVDs); magneto-optical media such as floptical disks; and hardware devices such as read-only memory (ROM), random access memory (RAM) and flash memory, which are specially configured to store and execute program instructions. Examples of the program instructions include not only machine language codes created by a compiler, but also high-level language codes that can be executed by a computer using an interpreter. The above hardware devices may be changed to one or more software modules to perform the processes of the present invention, and vice versa.

Although the present invention has been described above in terms of specific items such as detailed elements as well as the limited embodiments and the drawings, they are only provided to help more general understanding of the invention, and the present invention is not limited to the above embodiments. It will be appreciated by those skilled in the art to which the present invention pertains that various modifications and changes may be made from the above description.

Therefore, the spirit of the present invention shall not be limited to the above-described embodiments, and the entire scope of the appended claims and their equivalents will fall within the scope and spirit of the invention.

What is claimed is:

1. A method performed in a device for estimating information on a golf swing, the device comprising one or more processors and the method comprising the steps of:
    by the one or more processors, estimating a three-dimensional position of at least one joint of a user, in response to acquiring two or more two-dimensional photographed images of the user's golf swing taken from different directions, by deriving probability information on a two-dimensional position of the at least one joint of the user from each of the two or more two-dimensional photographed images using an artificial neural network model, and combining the derived probability information on the two-dimensional position of the at least one joint; and
    by the one or more processors, estimating information on the user's golf swing with reference to the estimated three-dimensional position of the at least one joint,
    wherein in the position estimating step, the derived probability information on the two-dimensional position of the at least one joint is included in a two-dimensional heat map for each of the two or more two-dimensional photographed images, and the three-dimensional position of the at least one joint of the user is estimated with reference to a three-dimensional heat map generated by projecting each of the two-dimensional heat maps into a three-dimensional space,
    wherein in the position estimating step, the three-dimensional position of the at least one joint of the user is estimated by preferentially considering an image from which the position of the at least one joint of the user is more likely to be accurately estimated, among the two or more two-dimensional photographed images, over an image from which the position of the at least one joint of the user is less likely to be accurately estimated, with reference to values of the two-dimensional heat maps, and
    wherein in the position estimating step, information on relative positions and directions of two or more cameras that take the two or more two-dimensional photographed images, respectively, is further acquired, and calibration for generating the three-dimensional heat map is performed on the basis of the information on the relative positions and directions of the two or more cameras.

2. The method of claim 1, wherein the artificial neural network model is light-weighted using depthwise convolution and pointwise convolution.

3. The method of claim 1, wherein the information on the golf swing is estimated separately for each partial motion constituting the golf swing.

4. The method of claim 1, wherein in the position estimating step, a three-dimensional position of a golf club is further estimated by deriving probability information on a two-dimensional position of the golf club from each of the two or more two-dimensional photographed images using the artificial neural network model, and combining the derived probability information on the two-dimensional position of the golf club, and
    wherein in the information estimating step, the information on the user's golf swing is estimated with further reference to the estimated three-dimensional position of the golf club.

5. The method of claim 1, wherein in the position estimating step, storage of each of the acquired two-dimensional photographed images is started when a posture of the user estimated on the basis of the derived probability information on the two-dimensional position of the at least one joint satisfies a predetermined storage start condition, and the storage of each of the acquired two-dimensional photographed images is ended when the estimated posture of the user satisfies a predetermined storage end condition.

6. A non-transitory computer-readable recording medium having stored thereon a computer program for executing the method of claim 1.

7. A device for estimating information on a golf swing, the device comprising one or more processors configured to:
estimate a three-dimensional position of at least one joint of a user, in response to acquiring two or more two-dimensional photographed images of the user's golf swing taken from different directions, by deriving probability information on a two-dimensional position of the at least one joint of the user from each of the two or more two-dimensional photographed images using an artificial neural network model, and combining the derived probability information on the two-dimensional position of the at least one joint; and
estimate information on the user's golf swing with reference to the estimated three-dimensional position of the at least one joint,
wherein the derived probability information on the two-dimensional position of the at least one joint is included in a two-dimensional heat map for each of the two or more two-dimensional photographed images, and the one or more processors are configured to estimate the three-dimensional position of the at least one joint of the user with reference to a three-dimensional heat map generated by projecting each of the two-dimensional heat maps into a three-dimensional space,
wherein the one or more processors are configured to estimate the three-dimensional position of the at least one joint of the user by preferentially considering an image from which the position of the at least one joint of the user is more likely to be accurately estimated, among the two or more two-dimensional photographed images, over an image from which the position of the at least one joint of the user is less likely to be accurately estimated, with reference to values of the two-dimensional heat maps, and
wherein the one or more processors are configured to further acquire information on relative positions and directions of two or more cameras that take the two or more two-dimensional photographed images, respectively, and to perform calibration for generating the three-dimensional heat map on the basis of the information on the relative positions and directions of the two or more cameras.

8. The device of claim 7, wherein the artificial neural network model is light-weighted using depthwise convolution and pointwise convolution.

9. The device of claim 7, wherein the information on the golf swing is estimated separately for each partial motion constituting the golf swing.

10. The device of claim 7, wherein the one or more processors are configured to further estimate a three-dimensional position of a golf club by deriving probability information on a two-dimensional position of the golf club from each of the two or more two-dimensional photographed images using the artificial neural network model, and combining the derived probability information on the two-dimensional position of the golf club, and
wherein the one or more processors are configured to estimate the information on the user's golf swing with further reference to the estimated three-dimensional position of the golf club.

11. The device of claim 7, wherein the one or more processors are configured to cause storage of each of the acquired two-dimensional photographed images to be started when a posture of the user estimated on the basis of the derived probability information on the two-dimensional position of the at least one joint satisfies a predetermined storage start condition, and cause the storage of each of the acquired two-dimensional photographed images to be ended when the estimated posture of the user satisfies a predetermined storage end condition.

* * * * *